US00PP25888P2

(12) United States Plant Patent
Miyazaki

(10) Patent No.: US PP25,888 P2
(45) Date of Patent: Sep. 8, 2015

(54) ***LOBELIA* PLANT NAMED 'SUNLOBE BULUCON'**

(50) Latin Name: *Lobelia erinus*
Varietal Denomination: Sunlobe Bulucon

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 70 days.

(21) Appl. No.: 13/998,600

(22) Filed: Nov. 15, 2013

(51) Int. Cl.
*A01H 5/02* (2006.01)

(52) U.S. Cl.
USPC ..... Plt./451

(58) Field of Classification Search
USPC ..... Plt./451
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Lobelia* plant named 'Sunlobe Bulucon', characterized by its mounding plant habit; vigorous growth habit; freely branching habit; dense and bushy plant form; freely flowering habit; long flowering period; and violet blue-colored flowers.

1 Drawing Sheet

Botanical designation: *Lobelia erinus*.
Cultivar denomination: 'SUNLOBE BULUCON'.

BACKGROUND OF THE INVENTION

The present invention relates to a new and distinct cultivar of *Lobelia* plant, botanically known as *Lobelia erinus* and hereinafter referred to by the name 'Sunlobe Bulucon'.

The new *Lobelia* plant is a product of a planned breeding program conducted by the Inventor in Higashiomi, Shiga, Japan. The objective of the breeding program is to create new mounding, freely-branching and bushy *Lobelia* plants with numerous and large attractive flowers.

The new *Lobelia* plant originated from a cross-pollination made by the Inventor in May, 2010 of a proprietary selection of *Lobelia erinus* identified as code number 10Lob18A-1, not patented, as the female, or seed, parent with a proprietary selection of *Lobelia erinus* identified as code number 10Lob18A-2, not patented, as the male, or pollen, parent. The new *Lobelia* plant was discovered and selected by the Inventor as a single flowering plant with the progeny of the stated cross-pollination in a controlled greenhouse environment in Higashiomi, Shiga, Japan in May, 2011.

Asexual reproduction of the *Lobelia* plant by vegetative cuttings in Higashiomi, Shiga, Japan since May, 2011 has shown that the unique features of this new *Lobelia* plant are stable and reproduced true to type in successive generations.

SUMMARY OF THE INVENTION

Plants of the new *Lobelia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunlobe Bulucon'. These characteristics in combination distinguish 'Sunlobe Bulucon' as a new and distinct *Lobelia* plant:

1. Mounding plant habit.
2. Vigorous growth habit.
3. Freely branching habit; dense and bushy plant form.
4. Freely flowering habit.
5. Long flowering period.
6. Violet blue-colored flowers.

Plants of the new *Lobelia* differ primarily from plants of the female parent selection in flower color as plants of the female parent selection have sky blue-colored flowers.

Plants of the new *Lobelia* differ primarily from plants of the male parent selection in temperature tolerance as plants of the new *Lobelia* are more high temperature-tolerant than plants of the male parent selection.

Plants of the new *Lobelia* can be compared to plants of *Lobelia erinus* 'Sunlobecosubu', disclosed in U.S. Plant Pat. No. 25,242. In side-by-side comparisons conducted in Higashiomi, Shiga, Japan, plants of the new *Lobelia* differed from plants of 'Sunlobecosubu' in the following characteristics:

1. Plants of the new *Lobelia* were shorter and broader than plants of 'Sunlobecosubu'.
2. Plants of the new *Lobelia* had larger leaves than plants of 'Sunlobecosubu'.
3. Plants of the new *Lobelia* had larger flowers than plants of 'Sunlobecosubu'.
4. Plants of the new *Lobelia* and 'Sunlobecosubu' differed in flower color as plants of 'Sunlobecosubu' had light violet blue-colored flowers.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the top of the sheet comprises a side perspective view of a typical flowering plant of 'Sunlobe Bulucon' grown in a container.

The photograph at the bottom of the sheet is a close-up view of typical flowers of 'Sunlobe Bulucon'.

DETAILED BOTANICAL DESCRIPTION

Plants used for the aforementioned photographs and following description were grown during the early summer in 15-cm containers in an outdoor nursery in Higashiomi, Shiga, Japan and under cultural practices typical of commercial *Lobelia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Lobelia erinus* 'Sunlobe Bulucon'.

Parentage:

*Female, or seed, parent*.—Proprietary selection of *Lobelia erinus* identified as code number 10Lob18A-1, not patented.

*Male, or pollen, parent*.—Proprietary selection of *Lobelia erinus* identified as code number 10Lob18A-2, not patented.

Propagation:

*Type cutting*.—Vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; white in color.

*Rooting habit*.—Freely branching.

Plant description:

*Plant and growth habit*.—Mounding plant habit; freely branching habit with lateral branches developing at potentially every node; dense and bushy plant habit; vigorous growth habit.

*Plant height*.—About 22.4 cm.

*Plant width*.—About 43.3 cm.

*Lateral branch description*.—Diameter: About 1.6 mm. Internode length: About 2.37 cm. Strength: Strong, flexible. Aspect: Upright to outwardly. Texture: Pubescent, rough. Color: Close to 137C.

Leaf description:

*Arrangement*.—Alternate, simple; sessile.

*Length*.—About 4.32 cm.

*Width*.—About 9.8 cm.

*Shape*.—Narrowly elliptic.

*Apex*.—Acute.

*Base*.—Attenuate.

*Margin*.—Serrate.

*Texture, upper and lower surfaces*.—Pubescent.

*Venation pattern*.—Pinnate.

*Color*.—Developing leaves, upper surface: Close to 137A. Developing leaves, lower surface: Close to 137C. Fully expanded leaves, upper surface: Close to N137C; venation, close to 139C. Fully expanded leaves, lower surface: Close to 138A; venation, close to 137C.

Flower description:

*Flower arrangement, habit and shape*.—Flowers typically arranged in terminal and lateral racemes; flowers held mostly outwardly; freely flowering habit with about five flowers per inflorescence and about 422 flowers developing per plant; flowers bilabiate with two upper petals and three larger lower petals.

*Fragrance*.—None detected.

*Natural flowering season*.—In Japan, plants of the new *Lobelia* flower from May until October; early flowering habit, plants begin flowering about three to four weeks after planting.

*Flower longevity on the plant*.—Longevity of individual flowers is highly dependent on temperature, flowers typically last about 10 to 14 days on the plant; flowers persistent.

*Flower length*.—About 1.57 cm.

*Flower diameter*.—About 2.11 cm.

*Flower tube length*.—About 8.6 mm.

*Flower tube diameter*.—About 4.3 mm.

*Flower buds*.—Length: About 14.6 mm. Diameter: About 4.5 mm. Shape: Club-shaped. Color: Close to 90A.

*Petals*.—Arrangement: Single whorl of five petals fused towards the base; two upper petals and three larger lower petals. Upper petals: Length, beyond throat: About 6.2 mm. Width: About 2.5 mm. Shape: Narrowly elliptic. Apex: Acuminate. Margin: Entire. Texture, upper and lower surfaces: Smooth, glabrous. Lower petals: Length, beyond throat: About 1.1 cm. Width: About 7 mm. Shape: Ovate. Apex: Mucronate to rounded. Margin: Entire. Texture, upper and lower surfaces: Smooth, glabrous. Color, upper petals: When opening, upper surface: Close to N89B. When opening, lower surface: Close to N89D. Fully opened, upper surface: Close to N89C. Fully opened, lower surface: Close to N89D. Color, lower petals: When opening and fully opened, upper surface: Close to N89B; towards the base, close to NN155C; basal spot, close to N89A. When opening and fully opened, lower surface: Close to N89D; towards the base, close to NN155C. Color, throat: Close to NN155C; spots, close to N89D. Color, tube: Distally, close to N89D; proximally, close to N89D and NN155C.

*Sepals*.—Arrangement: Single whorl of five sepals, fused at the base; star-shaped calyx. Length: About 8.9 mm. Width: About 1.3 mm. Shape: Narrowly deltoid. Apex: Acute. Margin: Entire. Texture, upper and lower surfaces: Slightly pubescent. Color, upper surface: Close to 137B tinted with close to 59A. Color, lower surface: Close to 137C tinted with close to 59A.

*Pedicels*.—Length: About 3.64 cm. Diameter: About 0.5 mm. Strength: Strong, flexible. Texture: Slightly pubescent. Color: Close to 137C.

*Reproductive organs*.—Stamens: Quantity per flower: Five. Stamen length: About 6.6 mm. Anther size: About 1 mm by 2 mm. Anther shape: Oblong, fused. Anther color: Close to N89B. Pollen amount: Moderate. Pollen color: Close to 155D. Pistils: Quantity per flower: One. Pistil length: About 8.2 mm. Stigma shape: Bi-lobate. Stigma color: Close to N89C. Style color: Close to 144D. Ovary color: Close to 144C.

*Fruits and seeds*.—Fruit and seed development have not been observed on plants of the new *Lobelia*.

Disease & pest resistance: Plants of the new *Lobelia* have not been noted to be resistant to pathogens and pests common to *Lobelia* plants.

Garden performance: Plants of the new *Lobelia* have been observed to have good garden performance and to tolerate wind, rain and temperatures ranging from about 5° C. to about 35° C.

It is claimed:

1. A new and distinct *Lobelia* plant named 'Sunlobe Bulucon' as illustrated and described.

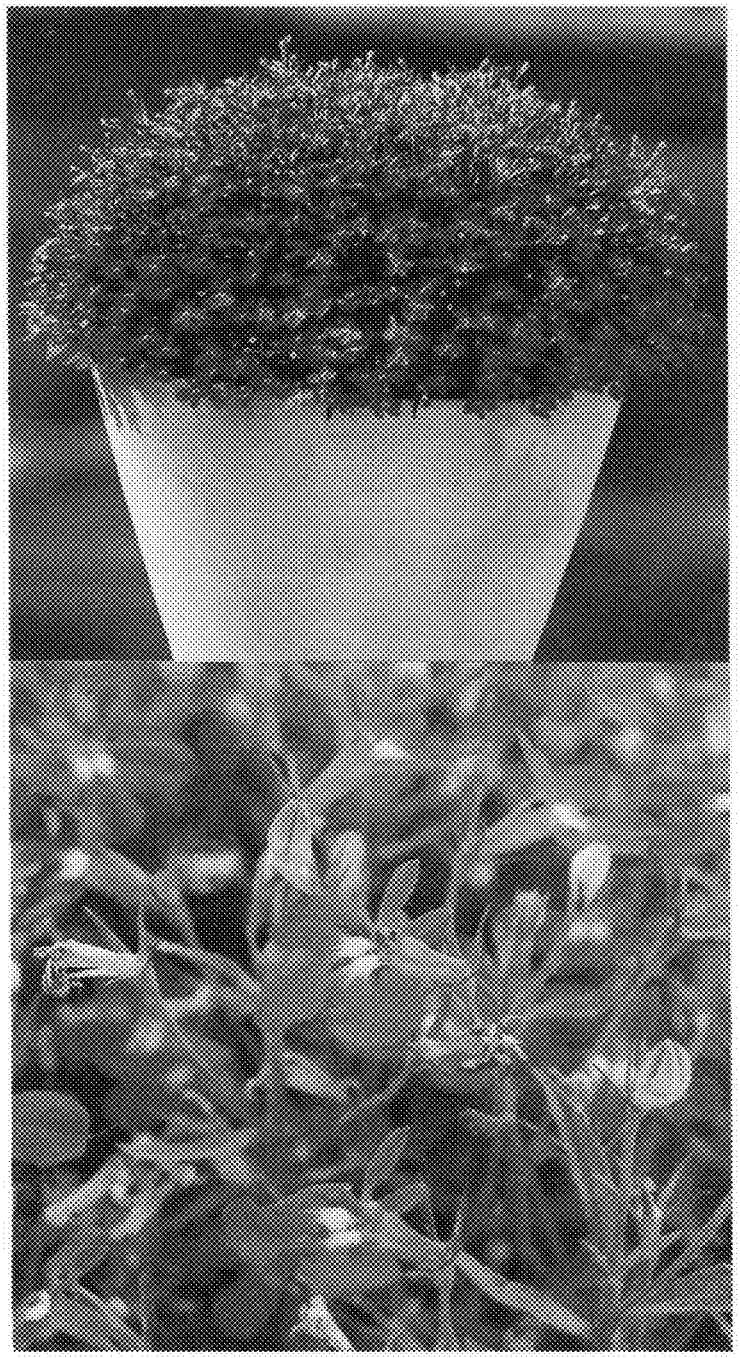

* * * * *